United States Patent [19]

Czerlinski

[11] 4,369,345

[45] Jan. 18, 1983

[54] METHOD OF AND APPARATUS FOR SELECTIVE LOCALIZED DIFFERENTIAL HYPERTHERMIA OF A MEDIUM

[76] Inventor: George H. Czerlinski, 9111 Forest View Rd., Skokie, Ill. 60203

[21] Appl. No.: 86,262

[22] Filed: Oct. 18, 1979

Related U.S. Application Data

[62] Division of Ser. No. 853,269, Nov. 11, 1977, abandoned.

[51] Int. Cl.³ .......................... H05B 6/06; A61N 1/42
[52] U.S. Cl. .......................... 219/10.43; 219/10.49 R; 219/10.57; 219/10.75; 219/10.79; 128/1.5; 128/399; 148/121
[58] Field of Search .......... 219/10.43, 10.41, 10.49 R, 219/10.75, 10.77, 10.65, 10.57, 10.67, 10.79; 148/108, 103, 105, 121; 313/325; 128/1.3, 1.5, 399, 422

[56] References Cited

U.S. PATENT DOCUMENTS 4,136,683 1/1979 Gordon ........................ 128/1.3 X
4,190,053 2/1980 Sterzer ............................ 128/399

OTHER PUBLICATIONS

Callen, "Thermodynamics", Section 14.6, on The Magnetocaloric Effect," published 1960.

Primary Examiner—B. A. Reynolds
Assistant Examiner—Philip H. Leung
Attorney, Agent, or Firm—Ratner & Prestia

[57] ABSTRACT

Apparatus generates a pulsed, alternating magnetic field which is coupled to magnetizable particles of submicron size dispersed in colloidal suspension in a medium. The frequency of the applied magnetic field is related to the size of the particles in such a manner as to maximize dissipative heat coupling to the medium. The differential temperature rise in the area of the medium surrounding the particles may be controlled by the concentration of the particles. Thus, defined temperature rises may be selectively produced in highly localized areas.

6 Claims, 8 Drawing Figures

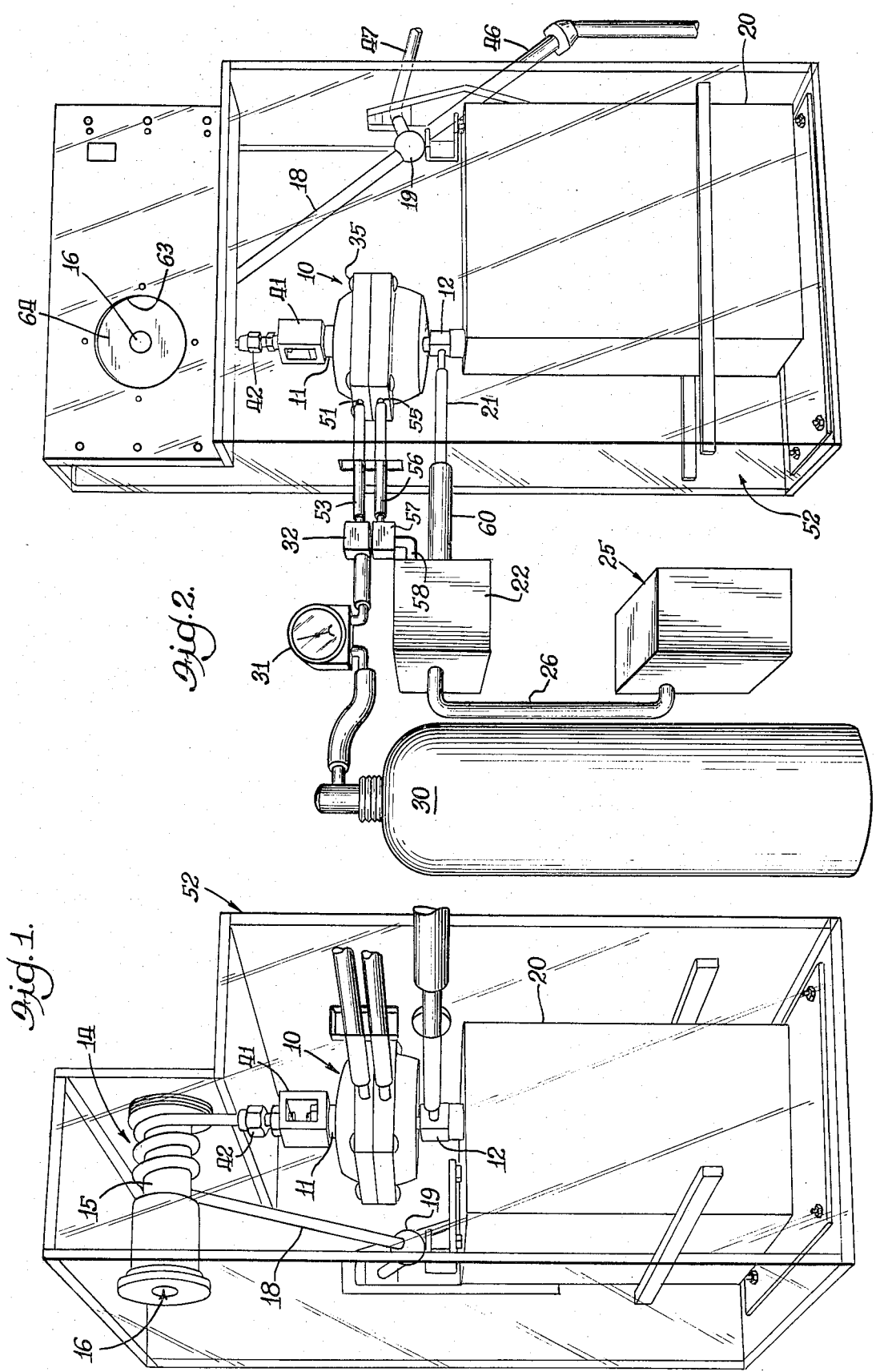

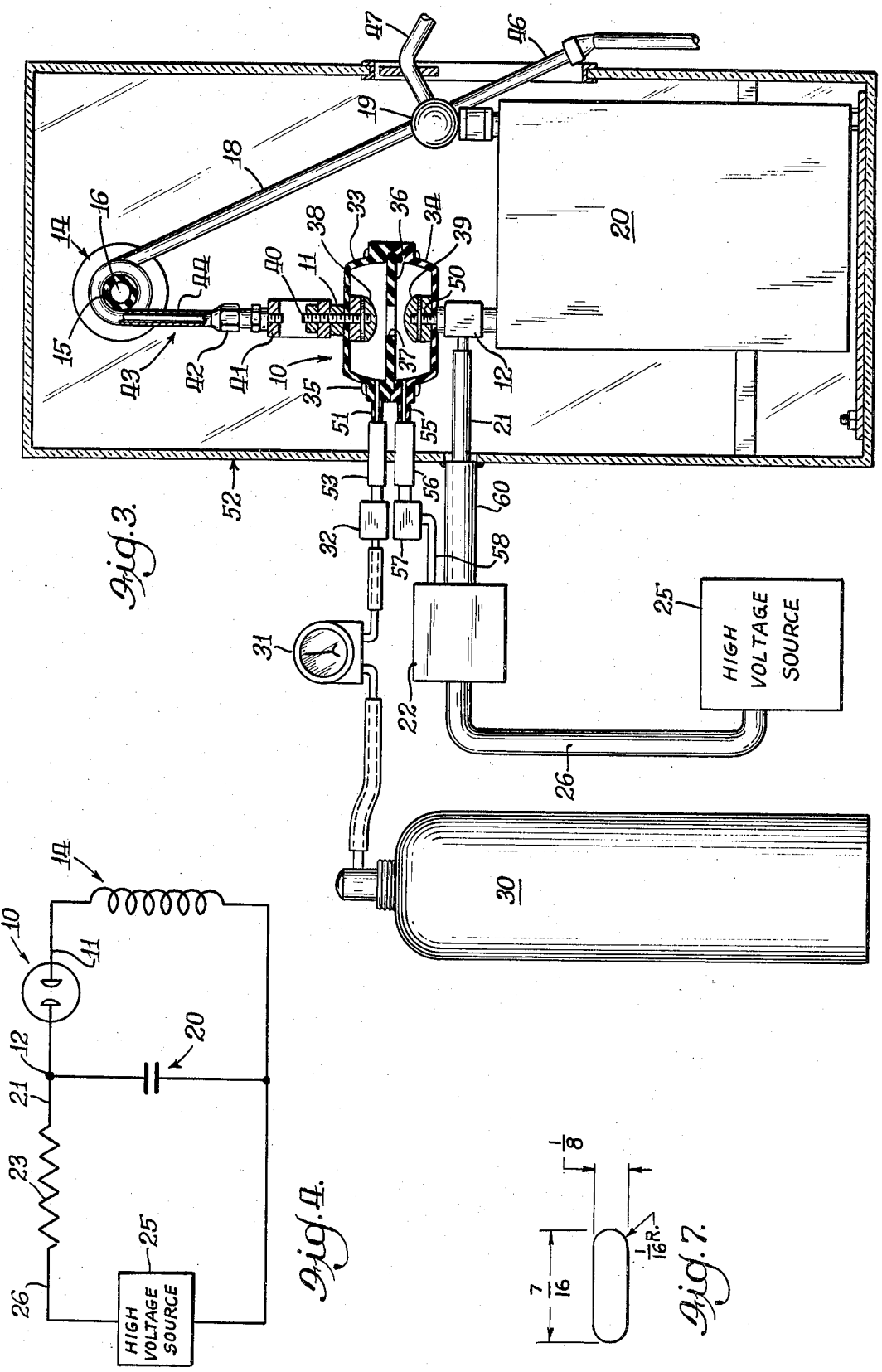

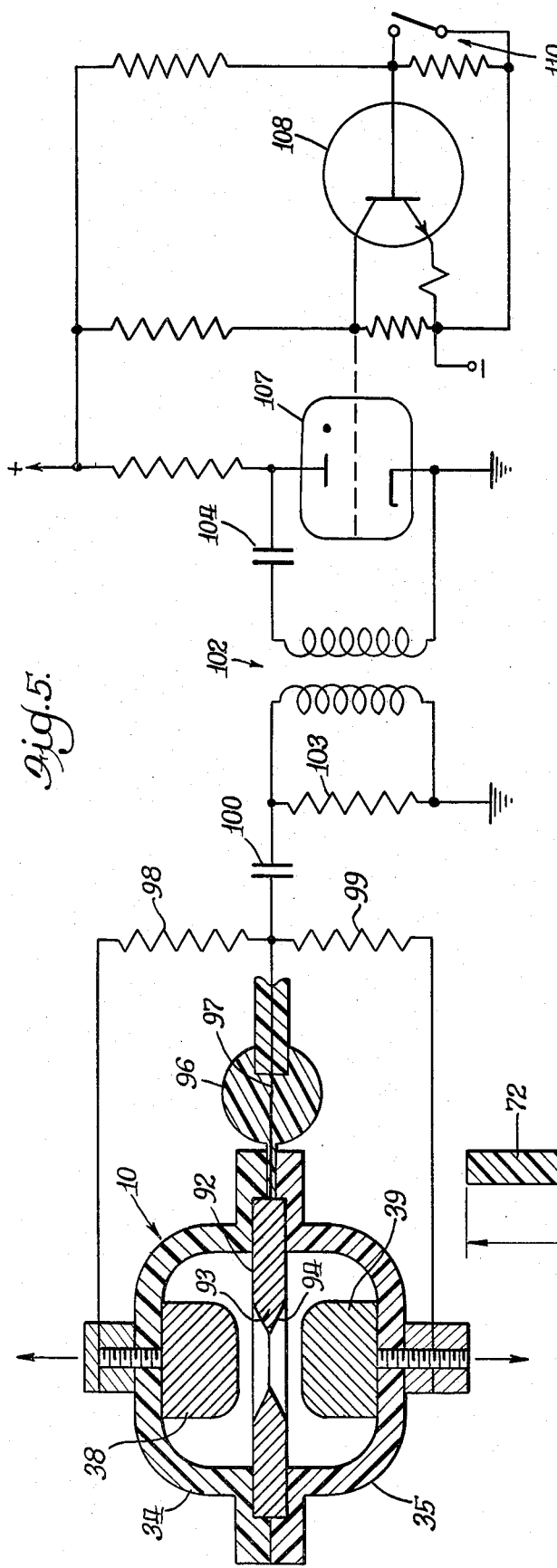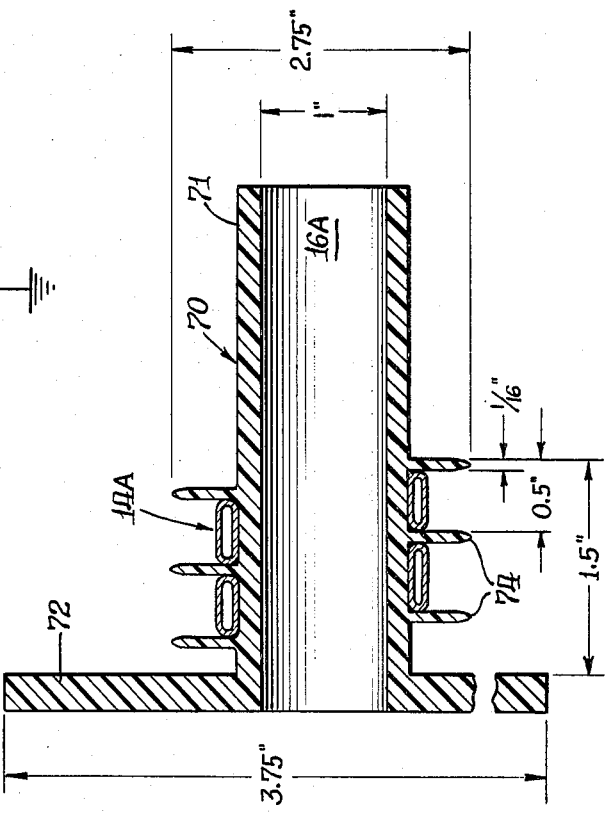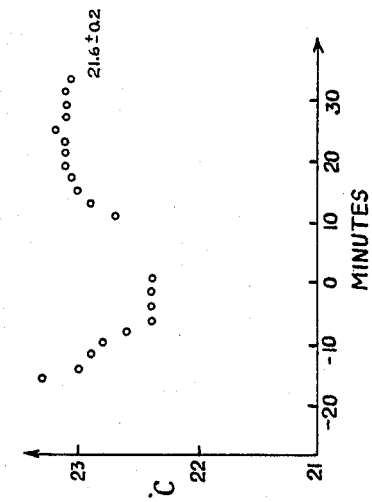

METHOD OF AND APPARATUS FOR SELECTIVE LOCALIZED DIFFERENTIAL HYPERTHERMIA OF A MEDIUM

The Government has rights in this invention pursuant to Grant No. BMS71-00826 awarded by the National Science Foundation.

This is a division, of application Ser. No. 853,269, filed Nov. 11, 1977 now abandoned.

BACKGROUND AND SUMMARY

The present invention relates to a method of and apparatus for selectively producing a temperature rise in a highly localized area of a medium. The medium may be heterogeneous, and the differential temperature rise may be controlled.

A phenomenon referred to as chemical relaxation was disclosed in 1954 by M. Eigen, *Discussions of the Faraday Society*, volume 17, pages 194–205. He described a method of producing a temperature rise using Joule's heating with a conducting electrolyte solution. In this method, typically, volumes of around 1 ml. of a homogeneous system are used, see also Czerlinski and Eigen, *Z. Elektrochem*, vol. 63, p. 652 (1959).

The method of the present invention is directed to producing differential hyperthermia to volumes much smaller than 1 ml. Further, the method is applicable to heterogeneous systems, such as cellular systems and tissues.

The method uses magnetizable particles which are very small in size, preferably in the order of 0.1–1.0 microns for biological applications, but generally in the range of 0.05–10 microns. Such magnetizable materials are intended to include both ferromagnetic and ferrimagnetic materials. Particles of the first size range are subcellular and can be selectively localized within the system to thereby achieve a highly localized hyperthermia. An external alternating magnetic field is applied to the particles. In the disclosed apparatus, the magnetic field is pulsed, and has a high magnetic field component but a relatively low electric field component.

With the particles in the preferred size range, coupling between the magnetic field and the surrounding matter becomes substantial. Further, by relating the frequency of the applied magnetic field to the particle size in a manner to be disclosed below, dissipative heat coupling from the small particles in the heterogeneous medium to the localized neighboring areas of the medium is maximized.

Other features and advantages of the present invention will be apparent to persons skilled in the art from the following detailed description of a preferred embodiment accompanied by the attached drawing wherein identical reference numerals will refer to like parts in the various views.

THE DRAWING

FIG. 1 is a perspective view of a portion of the apparatus according to the present invention for generating pulses of alternating magnetic fields, taken from the rear and right side;

FIG. 2 is a perspective view of the apparatus of FIG. 1 taken from the front and left side, and including other elements of the system, some of which are shown in diagrammatic form;

FIG. 3 is a front view of the system of FIG. 2 with the outer protective housing and the spark gap switch shown in vertical cross section;

FIG. 4 is a circuit schematic diagram of the magnetic field generator;

FIG. 5 is an illustration of an electronic embodiment for triggering the spark gap switch including a circuit schematic diagram and a vertical cross sectional view of a spark gap switch capable of being triggered electronically;

FIG. 6 is a vertical cross sectional view of a housing providing the sample or specimen tunnel and a preferred coil for maximizing magnetic field strength while reducing electric field strength of the applied field;

FIG. 7 is a diagrammatic view illustrating the dimensions of the cross section of the coil element of FIG. 6; and FIG. 8 is a graph illustrating hyperthermia produced according to the present invention.

DETAILED DESCRIPTION

Referring particularly to FIGS. 1–3, reference numeral 10 generally designates a spark gap switch or spark gap generator, as it is sometimes called. The spark gap switch includes a first terminal 11 (shown as the upper terminal in the drawing) and a second or lower terminal 12. The terminal 11 is electrically connected to a coil generally designated 14 in FIGS. 1 and 3 which is mounted on an insulating support 15 which is of tubular shape adjacent the coil 14 to provide a central generally cylindrical space 16. The space 16 is sometimes referred to as a "specimen tunnel," and it is used for the placement of samples or specimens under study, as will be more fully described below.

Electrically, the other terminal of the coil 14 is connected by means of a conductive tubular line 18 and a spherical conductive element 19 to the grounded terminal of a capacitor 20. The positive terminal of the capacitor is connected to the connector 12, which is also connected by means of a lead 21 to a charging resistor which is supported within a housing 22. The charging resistor is shown schematically at 23 in FIG. 4, as are the spark gap switch 10, coil 14, and capacitor 20. The other terminal of the charging resistor is connected to a high voltage supply 25, by means of an insulated conductor 26.

Referring now to FIG. 4, the high voltage source 26 charges the capacitor 20 through the charging resistor 23 until such time as the spark gap switch 10 creates a short or low-conductance path between the connectors 11, 12. At this time, the energy stored in the capacitor 20 is discharged through the spark gap switch 10 and the inductance coil 14. This is a very low-loss (that is, low resistance) circuit, and the capacitance value of capacitor 20 and inductance of coil 14 determine the frequency of oscillation of the resulting current flow. In other words, the capacitor 20 and coil 14 form a ringing circuit for an exponentially damped current having a frequency determined by the values of the circuit elements just indicated. The current flowing through the coil 14 creates a magnetic field in the specimen tunnel 16 for producing dissipative heating in a specimen placed therein as will be described below.

Returning now to FIGS. 1–3, a source of pressurized gas 30 is coupled through a pressure meter 31 and a manually actuated on/off valve 32 to the spark gap housing 10. Referring particularly to FIG. 3, the housing 10 is formed of complementary upper and lower sections 33, 34 which may be formed from a transparent plastic, such as acrylic having properties of physical strength and good electrical insulation. The upper and lower sections 33, 34 of the housing may be secured together by insulating threaded fasteners 35. A center plate 36 forms a separator, and it is provided with a central aperture 37 which is aligned with first and second electrodes 38, 39. The electrode 38 is coupled by means of a threaded fastener 40 to the terminal 11 and a square connector 41, the upper portion of which is directly connected at 42 to a pair of concentric tubular elements generally designated 43. The outer tubular element 44 forms the previously described coil 44; and thereafter, it forms the connector 18. The spherical connector 19 has connected to it a first conduit 46 for receiving a coolant such as water and forcing it in the outer annular region between the outer conductor 44 and the inner tube or conduit. The coolant is thus forced to cool the coil 14 and is routed to the connector 42 where it returns through the inner conduit to the connector 19 and is discharged through a conduit 47.

Returning again to FIG. 3, the lower electrode 19 is connected by means of a threaded fastener 50 to the connector 12 which has already been described.

The spark gap housing 10 is provided with an inlet 51 which is coupled through an outer housing 52 by means of a tubular conduit 53 to the on/off valve 32. The spark gap housing 10 also includes an outlet for discharge conduit 55 which is coupled through the housing 52 by means of a conduit 56 to a manually adjustable reducing valve 57. The housing 52 is preferably made of a material having high dielectric strength for enclosing the capacitor, the inductor and the switch. The outlet of the valve 57 is coupled by means of a conduit 58 to the housing 22 for the charging resistor 23.

A tubular discharge conduit 60 is connected between the resistor housing 22 and the main housing 52 surrounding the insulated connector 21.

The gas within the source 30 preferably has a very low moisture content, such as commercially available "artificial" air, having 1 ppm each of $CO_2$ and $H_2O$. Other gases of high dielectric strength may equally well be employed.

In operation, the valve 32 is first turned on, admitting air from the source 30 to the inlet port 51 of the spark gap housing 33, 34, to pressurize the spark gap generator. The high voltage source 25 is permitted to charge the capacitor 20 through the charging resistor 22. As long as the pressure within the spark gap generator 10 is above a predetermined limit, for the particular electrodes and electrode spacing used, and for the value of the capacitor and charging voltage, the capacitor remains charged. When it is desired to discharge the capacitor, the reducing valve 57 is adjusted to permit gas to flow from the spark gap generator, thereby reducing the pressure and causing an arc between the electrodes 38, 39, to discharge the energy stored in the capacitor 20 through the coil 14.

The gas from the reducing valve 57 is used to purge the resistor housing 22 and the main housing 52, thereby maintaining the charging resistor 23, capacitor 20, spark gap 10 and coil 14 in an atmosphere having very low moisture content. This reduces the possibility of spurious arcing and the effects of corona discharge. The air is discharged from the main housing 52 through an annular opening designated 63 in FIG. 2 which is located adjacent the rear flange 64 of the tubular mount 15 for the coil 14.

The high voltage source 25 may be a commercially available unit such as the model 60N120, manufactured by Spellman High Voltage Electronics Corp., of Bronx, New York. It is rated as 60 KV. 2 mA. The input is transformer-insulated from the 110 V. 60 Hz line. A ground cable of the source 25 preferably is connected through an inductor to a good ground such as a water pipe; and a heavy copper cable (not shown) connects the water pipe to the ground terminal of the capacitor 20.

The resistor housing 22 may also be made from acrylic plastic, and the resistors are preferably mounted on posts of a material having high insulating properties such as "Delrin," using brass holders. The total resistance value may be 30 megohms to utilize the full rating of the 60 KV. capacitor. Conventional techniques such as polishing of metal parts are used to reduce corona effects.

The capacitor 20 is rated for 60 KV., as mentioned, and for 0.5 microfarads and 20 milliohms nominal. It is desirable to minimize the conductive length between the positive terminal of the capacitor and the spark gap generator, and between the inductor and the negative terminal of the capacitor because this might add to the inductance of the ringing circuit.

The spark gap electrodes 38, 39 may be brass with tungsten surfaces; and the separator plate 36 may be Teflon. The aperture 37 is used to direct the resulting spark between the tungsten surfaces of the electrodes.

The distance between electrodes is set for operation between 30 and 60 KV., depending upon the application, at pressures up to 60 psi within the housing of the spark gap generator.

The coil 14 may have 2.6 turns, and an inductance of about 300 nH. (although the embodiment of FIG. 6, to be described, has an inductance of about 400 nH). If, as in the case of FIG. 3, the coil 14 is constructed from copper tubing having an outer diameter of $\frac{1}{4}$ in., the diameter of the cylindrical central portion 15 of the holder may be 1.5 in.

Turning now to the embodiment of the field-producing coil shown in FIG. 6, the coil is designated 14A, and it is supported on a machined Teflon holder generally designated 70 which includes a tubular portion 71 for providing the specimen tunnel 16A, and a mounting flange 72. Helical Teflon separators 74 are milled in the support 70 to separate the turns of the coil 14A which is formed from a flattened copper tubing. The ends of the coil are formed into smooth transition with the connecting copper tubes. In this embodiment, as illustrated in FIG. 7, the longer outer dimension of the flattened tubing is 7/16 in., and the shorter dimension is $\frac{1}{8}$ in. The radius is 1/16 in. Preferably, the coil is gold plated.

It is contemplated that various experimental test units or modules may be used with the apparatus of the present invention. These test units, for the most part, would be adapted to be inserted into the specimen tunnel 16 which has an opening of approximately one inch in diameter. Such test units might include a thermometric test unit having an alcohol thermometer, a small polycarbonate sample tube (for quasi-homogeneous systems) with a coaxial tube holder with air ventilation for observation time ranges of 1–100 minutes; an optical test unit having a pencil beam from a continuous wave laser and a photodiode detector for the purpose of determining the density of the magnetic particles thereby being able to measure and control their concentrations in the medium; a microscope slide unit for observing cell systems in a water medium that will sustain cellular functions and maintain osmotic balance whereby the magnetic particle concentration is inserted by the usual technique of pipetting the homogeneous suspension into the medium or by injecting subcutaneously into an organism; a microspectrophoto-(fluoro)-metric unit for direct observation of cellular changes;, and so on.

Referring now to FIG. 5, there is shown an electronic system for triggering the spark gap switch to generate the arc. The spark gap switch is generally designated 10, again; and it includes upper and lower sections 34, 35 and upper and lower electrodes 38, 39, which may be constructed as disclosed above and connected in circuit as already indicated. A central separator 92 is supported between the housing sections 34, 35, and it includes an upper frusto-conical surface 93 facing the upper electrode 38, and a lower frusto-conical surface 94 facing the lower electrode 39 for focusing and concentrating the field between the two electrodes. The separator 92 in this embodiment is a conductive element; and it is intended to be maintained at a potential midway between the potential difference across the electrodes 38, 39. A dielectric member 96 couples an insulated wire 97 to the separator 92. The wire 97 is connected to the upper and lower electrodes 38, 39 by means of a pair of high resistors 98, 99 respectively, which resistors form a voltage dividing network. A capacitor couples the connector 97 to the secondary of a pulse transformer 102. A resistor 103 is also connected across the secondary of the transformer 102. The primary of the transformer 102 is connected in series with a capacitor 104 across a thyratron 107. The plate of the thyratron is biased to a positive voltage, and the grid is connected to the collector of a transistor 108. The emitter of the transistor 108 is connected to a negative bias supply. A switch 110 is connected between the base and emitter junctions of the transistor 108.

When the switch 110 is closed, the transistor is non-conducting; and the collector goes positive, causing the thyratron to fire. A resulting negative pulse is coupled through the pulse transformer 102 and capacitor 100 to the insulated wire 97 to cause the conducting spacer 92 to be reduced in voltage, thereby initiating an arc between the electrodes 38, 39. When the switch is opened, the transistor conducts, and a negative voltage is applied to the thyratron to drive it to cut off.

Although theoretical design considerations will be helpful in designing the coil used for generating the magnetic field, and persons skilled in the art will be readily able to design such a coil depending upon the desired frequency of the excitation current and the required inductance to obtain a given frequency, I have found that the preferred procedure is to actually measure the inductance. One of the reasons that the observed or measured inductance may vary from a computed or theoretical inductance is the circuit inductance resulting from the spark gap itself since it is in series with the coil inductance and will, therefore, to some extent affect the resonant frequency of the discharge circuit.

Theoretical Basis of Method

Using the apparatus disclosed above, the method of producing selective, localized hyperthermia will now be discussed in its theoretical aspects. This method employs the absorption of magnetic energy. Coupling between the magnetic field and matter becomes substantial only when ferromagnetic (or ferrimagnetic) domains are present. Such domains consist of approximately $10^6$ to $10^9$ molecules. A range of particle sizes for biological applications is 0.05–1.0 microns, although the invention has broader application. Particles of this size are subcellular and might be guided into highly localized areas or even specific cells thereby permitting highly selective hyperthermia.

Adiabatic (i.e., constant entropy) magnetization (involving the magnetocaloric effect) is a phenomenon defined most suitably in the derivation of H. B. Callen, *Thermodynamics,* Wiley, New York, 1960) p. 255. The initial expression for the effect is given by:

$$dT = \left(\frac{\delta T}{\delta H_e}\right)_{P,S} dH_e \quad [1]$$

where $H_e$ is the applied (external) field strength in A/m, T the temperature in °K., P the pressure and S the entropy. Upon rearrangement and with the appropriate thermodynamic Maxwell equations one obtains $$dT = -\frac{TV}{C_{P,H_e}}\left(\frac{\delta J}{\delta T}\right)_{P,H_e} dH_e \quad [2]$$

It is V the volume in $m^3$, C the heat capacity in J/deg. J the magnetization of the material in $Vs/m^2$. The latter is also given by $$J = \mu° \chi_{T,P} H_e \quad [3]$$

for $H_e$ approximately H (see below) and with $\mu° = 1.26 \times 10^{-6} VsA^{-1}m^{-1}$ and $\chi$ the magnetic susceptibility (paramagnetic region; a number). According to the law of Curie and Weiss, $$\chi_{T,P} = \frac{C_c}{T - T_c} \quad [4]$$

with $C_c$ the Curie Constant and $T_c$ the Curie Temperature—one obtains $$\left(\frac{\delta \chi_{T,P}}{\delta T}\right)_{P,H_e} = -\frac{C_c}{(T-T_c)^2} = -\frac{\chi^2_{T,P}}{C_c} \quad [5]$$

Assuming that $H_e$ is close enough to the local field strength H one may integrate for the three regions:

$$T > T_c \; \Delta T = \frac{\mu° TVC_c}{2C_{P,H_e}(T-T_c)^2} H_e^2 \quad [6]$$

$$T = T_c \; \Delta T = \frac{\mu° TV\chi^2_{T_c,P}}{2C_{P,H_e}C_c} H_e^2 \quad [7]$$

$$T < T_c \; \Delta T = \frac{\mu° TVC_c}{2C_{P,H_e}(T_c-T)^2}(H_e^2 - H_s^2) \quad [8]$$

Equation [8] applies only for $H_e > H_s$, the field strength necessary for magnetic saturation at temperature T.

Equation [7] applies to a range of 5°–15° C. around the Curie temperature of the mediator. There is a rather flat maximum to the heating curve, and optimum heating takes place within this range. Thus, the greatest dissipative heating occurs if the particles are selected to have a Curie point which is approximately one-half of the desired temperature rise above the temperature of the medium. This consideration preferably governs the selection of the mediator particles depending upon the application.

The time dependent (instantaneous) energy density is given by $$Q'(t) = \frac{\Delta T(t)}{V/C_{P,He}} = \alpha H_o^2 \sin^2 \omega' t \quad [9]$$

with the following definitions $$\alpha = \frac{\mu^\circ TC_c}{2(T-T_c)^2}; \omega' = 2\pi f \quad [10]$$

Furthermore, $H_o$ is the amplitude of the local field strength, and f is the frequency of the applied alternating magnetic field. The heating energy during the stationary state of oscillation varies with time according to $$Q'(t)_{SS} \cong \alpha H_e^2 \left( \frac{1}{2} + \frac{1}{2} \sin 2\omega' t \right) \quad [11]$$

assuming no losses. This is an approximation.

The generalized dissipative expression (6)

$$tg\phi = \omega\tau \quad [12]$$

contains the imposing circular frequency, here defined as $$\omega = 2\omega' \quad [13]$$

and the dissipative time constant, $\tau$, here given by (7)

$$\tau = \tau_D = \frac{r_M^2}{\pi^2 D_h} \quad [14]$$

with $r_M$ the radius of the spherical isotropic homogeneous magnetic particle, given in the units m, and $D_h$ the heat diffusion constant of the surrounding medium in $m^2 s^{-1}$. One thus obtains $$tg\phi = \omega\tau = \frac{4fr_M^2}{\pi D_h} \quad [15]$$

Maximum dissipation is given by:

$$tg\phi = 1 \longrightarrow f_M = \frac{\pi D_h}{4r_M^2} \quad [16]$$

defining a special frequency $f_M$ which is a frequency of maximum dissipative loss. It will be observed from Equation [16] that the frequency $f_M$ is inversely proportional to the square of the mean radius of the particles.

In the stationary state, the dissipative energy flux density is described by (compare Equation [8]):

$$\dot{Q}_{irr}' = \alpha f H_o^2 \cos\phi \sin\phi \quad [17]$$

Using the well-known trigonometric relationship $$\cos\phi \sin\phi = \frac{1}{2} \sin 2\phi \quad [18]$$

at frequency $f_M$, $\phi = \pi/4$ and eq. [18] leads to $\frac{1}{2}$; Equation [17] becomes for this special case $$\dot{Q}_{irr}'' = \frac{1}{2}\alpha f H_o^2 \quad [19]$$

If $\Delta t$ is the duration of the stationary state in s the associated temperature rise is given by $$\Delta T_{bulk} = \frac{\dot{Q}_{irr}' \Delta t V_M}{V_o(C_M' V_M/V_o + C_S' V_S/V_o)} \quad [20]$$

$C_M'$ and $C_S'$ are the specific heats for the magnetic material and the solvent, respectively, given in $Jm^{-3}deg^{-1}$. $V_M$ and $V_S$ are the partial volumes of magnetic material and solvent, respectively. The total volume is then given by $$V_O = V_M + V_S \quad [21]$$

Equation [20] represents an approximation for multicomponent alloys as magnetic materials.

During the stationary state there is also a temperature profile around the spherical particle (9):

$$\Delta T_{SS} = \frac{\dot{Q}_{irr}' r_M^3}{3\lambda_h r} \text{ for } r \geq r_M \quad [22]$$

Heating from hysteresis losses will be considered for comparison. An expression similar to Equation [20] is obtained:

$$\Delta T_{hys} = \frac{(\phi J\, dH)_{hys} f \Delta t V_M}{V_o(C_M' V_M/V_o + C_S' V_S/V_o)} \quad [23]$$

The integral in the numerator corresponds to the "BH-Product" reported primarily for hard magnetic materials; it is to be given in $Jm^{-3}$ for one full cycle.

Experimental Results

Using the apparatus described above, the discharge of the spark gap was controlled by a setting of a high voltage meter and a current meter on the high voltage supply, described above. By controlling the pressure at the reducing valve located downstream of the spark gap, as illustrated, the discharge voltage may be controlled to within 5%. The charging time constant may be as high as 15 seconds. A polycarbonate test tube (in an insulating holder) was used to place the samples in the specimen tunnel.

In one test, 300 mg alloy powder (La-alloy) are transferred into an Agate mortar and mixed thoroughly with 100 mg of sodium oleate (supplied by Sigma Chemical Co.) until the mixture became a homogeneous powder. Then, 0.7 cm³ of water was added incrementally from a graduated syringe. A homogeneous suspension was produced by thoroughly mixing with the pestle in the mortar.

Referring now to Table I, the left column indicates different particulate materials prepared in this manner. The particles have a mean diameter of 5 microns.

TABLE I

| Particulate Material | Coil turns | $U_o$ kV | $H_o$ MA/m | $\frac{V_M}{V_o}$ | $\Delta T$ comp. | $\Delta T$ obs. | T °K. |
|---|---|---|---|---|---|---|---|
| Alnico 5 | 2.5 | 60 | 5 | 0.1 | 0.5 | 0.25 | 295. |
| La-alloy | 2.5 | 60 | 5 | 0.1 | 1.5 | 0.2 | 296 |
| La-alloy | 2.5 | 60 | 5 | 0.1 | 1.25 | 0.2 | 295 |
| La-alloy | 0.98 | 10 | 11 | 0.09 | 5.2 | 0.2 | 295 |

TABLE I-continued

| Particulate Material | Coil turns | $U_o$ kV | $H_o$ MA/m | $\frac{V_M}{V_o}$ | ΔT comp. | ΔT obs. | T °K. |
|---|---|---|---|---|---|---|---|
| La-alloy | 0.98 | 20 | 22 | 0.09 | 20.4 | 0.4 | 295 |

To measure temperature rises, alcohol thermometers were employed. These thermometers were 11 cm long over all and the stem measured 9 cm. and 3 mm. in diameter. The "bulb" portion of the end of the stem is 2 cm. long. The holding tube had an inner diameter of 8 mm. and an outer diameter of 10.9 mm. The "bulb" portion of the thermometer remained fully immersed in the suspension, and its total volume is 0.14 cm.$^3$—or approximately 20% of the volume of the suspension.

FIG. 8 represents typical measurements using the apparatus disclosed above, ten pulses of the alternating field were generated starting at zero with a frequency of 0.3 MHz. The material or mediator is LaMn$_2$Ge$_2$ having a mean particle size of 10 microns, and a concentration of about 10% (by volume) which obviously can be controlled since the weight of the particles in the suspension is known prior to forming the homogeneous mixture. Of course, depending upon the various sizes of the particles that will be used, concentration determinations can also be made by well-known electron microscopy techniques. The circles define the response curve, which evidences a slight time lag caused by the thermometric detector.

Referring again to Table I, the observed temperature rises were below the computed (or theoretically expected) temperature rises; and this discrepancy is ascribed to the large particle size and the broad particle size distribution used.

In summary, the experiments were conducted with a frequency of 0.3 MHz., whereas computations subsequently indicated that a frequency of about 0.02 MHz should have been used, considering the effects of the inverse square law disclosed above. The last two rows of Table I indicate that the observed temperature rise does not vary quadratically with the field strength, but only linearly. However, the magnetic field strength is very large and magnetic saturation may have been approached. Once magnetic particle concentration was determined using, for example, the electron microscopy technique previously mentioned, and thereby controlled, location within the medium has, simultaneously, been determined for the reason that local concentrations can be observed in smaller volumes or compartments of the medium or cell system and not solely within the medium as a whole. Location can also be determined by using well-known radioactive isotope techniques.

Having thus disclosed in detail preferred embodiments of the invention, persons skilled in the art will be able to modify certain of the structure which has been disclosed and to substitute equivalent materials for those described while continuing to practice the principle of the invention; and it is, therefore, intended that all such modifications and substitutions be covered as they are embraced within the spirit and scope of the appended claims.

I claim:

1. A method of producing localized hyperthermia in a medium having an ambient temperature, including the steps of: placing in said medium a quantity of particles of a magnetizable material having a Curie point approximately one-half the desired temperature rise above said ambient temperature of said medium, and a predetermined median radius; and applying an alternating magnetic field to said particles at a frequency inversely related to the square of said median radius of said particles to maximize the dissipated heat coupling to the localized areas of said medium surrounding said particles.

2. The method of claim 1 further comprising the step of dispersing said particles in said medium at a known concentration to induce a predetermined temperature rise in said medium.

3. The method of claim 2 wherein the median radius of said particles is in the range of 0.05–1.0 microns.

4. The method of claim 1 wherein said medium is heterogeneous and at least partially fluid.

5. The method of claim 1 wherein said field is characterized in having a high magnetic field strength and a relatively low electric field strength.

6. The method of claim 1 further comprising the step of generating said magnetic field by controlling the discharge of energy stored in a capacitor through a coil; and placing said medium and said particles in the center of said coil.

* * * * *